United States Patent [19]

Horodysky et al.

[11] Patent Number: 4,557,845

[45] Date of Patent: Dec. 10, 1985

[54] ALKOXYLATED AMINE-PHOSPHITE REACTION PRODUCT AND LUBRICANT AND FUEL CONTAINING SAME

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 561,413

[22] Filed: Dec. 14, 1983

[51] Int. Cl.$^4$ .................. C10M 1/32; C10M 1/46
[52] U.S. Cl. .................. 252/49.9; 252/32.5; 260/921; 260/970
[58] Field of Search .................. 252/49.9, 32.5; 260/921, 970

[56] References Cited

U.S. PATENT DOCUMENTS

| | | | |
|---|---|---|---|
| 2,574,516 | 11/1951 | Walter et al. | 252/49.9 X |
| 2,635,112 | 4/1953 | Fields | 252/49.9 X |
| 2,847,442 | 8/1958 | Sallman | 252/49.9 X |
| 3,238,277 | 3/1966 | Sigan et al. | 252/49.9 X |
| 3,321,401 | 5/1967 | Ford et al. | 252/49.9 X |
| 3,553,131 | 1/1971 | Hepplewhite et al. | 252/49.9 X |
| 3,677,943 | 7/1972 | Nnadi | 252/49.9 X |
| 3,718,588 | 2/1973 | Bellos et al. | 252/32.5 |
| 4,132,657 | 1/1979 | Verdicchio et al. | 252/49.9 X |

Primary Examiner—Jacqueline V. Howard
Attorney, Agent, or Firm—Alexander J. McKillop; Michael G. Gilman; Van D. Harrison, Jr.

[57] ABSTRACT

Products of reaction between a 2-hydroxyalkyl alkylamine or certain higher oxylated members, and a dihydrocarbyl phosphite have been found to be effective friction reducers and fuel reducing additives for internal combustion engines when such products are compounded with lubricants and liquid fuels.

25 Claims, No Drawings

ALKOXYLATED AMINE-PHOSPHITE REACTION PRODUCT AND LUBRICANT AND FUEL CONTAINING SAME

BACKGROUND OF THE INVENTION

1. Field of the Invention:

This invention relates to novel products of reaction and to their use as lubricant and fuel additives. More particularly, it relates to products of reaction between alkoxylated amines and dihydrocarbyl phosphites and to their use in the stated media.

2. Discussion of the Prior Art:

The metal surfaces of machinery or engines operating under heavy or normal loads wherein metal is undergoing metal to metal contact even when being lubricated. Thus, there is always metal wear which can be excessive, since lubricants often used to protect metal surfaces do not completely prevent wear at the points of metal to metal contact. Consequently, the performance of the machine or engine will suffer, and in aggravated cases the machine or engine may become completely inoperative from excessive wear caused by the friction.

There have been many attempts to devise additive systems to improve the friction and antiwear properties of a lubricant. The phosphate derivatives of the present invention are believed to be capable of overcoming some of the deficiencies of prior art additives and to provide lubricating oil and fuel compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 4,356,097 teaches an engine crankcase lubricating oil containing a dihydrocarbyl hydrocarbylphosphonate, which oil exhibits reduced friction.

U.S. Pat. No. 2,982,727 discloses lubricating oil compositions containing certain salts of oxygen-containing esters of phosphorus. The esters are phosphonates similar to those described in U.S. Pat. No. 2,758,971.

However, no art is known that teaches or suggests the phosphate ester of the present compositions.

SUMMARY OF THE INVENTION

In accordance with the invention, there are provided products of reaction made by reacting (1) an alkoxylated hydrocarbylamine of the formula

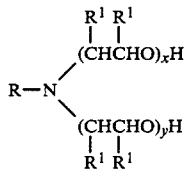

wherein R is a $C_6$ to $C_{30}$ hydrocarbyl group, $R^1$ is hydrogen or a $C_1$ to $C_6$ hydrocarbyl group, preferably a $C_1$ to $C_6$ alkyl group, and x and y are from 0 to about 10, preferably from about 1 to about 3, with the understanding that at least one, and preferably both of x and y will be at least 1, (2) a phosphite of the formula

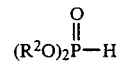

wherein $R^2$ is a $C_1$ to $C_6$ hydrocarbyl group, preferably an alkyl group.

The invention also provides lubricant and liquid fuel compositions containing the product and a method of reducing fuel consumption of an internal combustion engine by lubricating, fueling or lubricating and fueling said engine with the appropriate lubricant and fuel composition.

As used herein "hydrocarbyl", as has been stated, is preferably an alkyl group. It may also be selected from an aryl, alkaryl, aralkyl, alkenyl, cycloalkyl or cycloalkenyl group.

DESCRIPTION OF SPECIFIC EMBODIMENTS

The compounds of the invention are made by reacting the alkoxylated amine with the phosphite. The reaction is slow enough to permit mixing the reactants together and heating the mixture to effect reaction. Other means, as by slowly adding one to the other, heated reactant, can be used. In general, the reaction conditions are not critical, the temperatures ranging from about 80° C. to about 200° C., preferably from about 100° C. to about 260° C. Times of reaction will, on the average, be from 1 to 20 hours.

Reaction proportions are not critical, because effective products are obtained using a wide range of concentrations of phosphite relative to the concentrations of the amine. Thus, a product effective for the purposes of this invention can be made by proportioning the reactants so that from about 5% to about 100% of the amine hydroxy group react with the phosphite. Preferably, from about 35% to about 95% of the hydroxy groups are so reacted.

The useful alkoxylated amines include
2-hydroxylethylhexylamine, 2-hydroxyethyloctylamine,
2-hydroxyethyldodecylamine, 2-hydroxyethyltetradecylamine,
2-hydroxyethylpentadecylamine, 2-hydroxyethyleicosylamine,
2-hydroxyethyltriacontylamine, 2-hydroxyethyloleylamine,
2-hydroxyethyltallowamine, 2-hydroxyethylsoyamine,
bis(2-hydroxyethyl)hexylamine, bis(2-hydroxyethyl)octylamine,
bis(2-hydroxyethyl)dodecylamine, bis(2-hydroxyethyl)tetradecylamine,
bis(2-hydroxyethyl)pentadecylamine, bis(2-hydroxyethyl)eicosylamine,
bis(2-hydroxyethyl)triacontylamine, bis(2-hydroxyethyl)oleylamine,
bis(2-hydroxyethyl)tallowamine, bis(2-hydroxyethyl)soyamine,
2-hydroxylpropylhexylamine, 2-hydroxypropyloctylamine,
2-hydroxypropyldodecylamine, 2-hydroxypropyltetradecylamine,
2-hydroxypropylpentadecylamine, 2-hydroxypropyleicosylamine,
2-hydroxypropyltriacontylamine, 2-hydroxypropyloleylamine,
2-hydroxypropyltallowamine, 2-hydroxypropylsoyamine, bis(2-hydroxypropyl)hexylamine, bis(2-hydroxypropyl)octylamine,
bis(2-hydroxypropyl)dodecylamine, bis(2-hydroxypropyl)tetradecylamine,
bis(2-hydroxypropyl)pentadecylamine, bis(2-hydroxypropyl)eicosylamine,
bis(2-hydroxypropyl)triacontylamine, bis(2-hydroxypropyl)oleylamine,
bis(2-hydroxypropyl)tallowamine, bis(2-hydroxypropyl)soyamine and mixtures thereof. Also included are the comparable members wherein in the above formula at least one of x and y is at least 2, as for example, 2-hydroxyethoxyethylhexylamine.

The preferred phosphites are the dimethyl, diethyl, dipropyl, dibutyl, diamyl and dihexyl phosphites. Mixtures may also be used.

The exact structures of the products of this invention are not known and are therefore referred to in the specification and appended claims as products of reaction, reaction products or an equivalent expression. The reaction products can range from the simple to the complex, each such product comprising a mixture of compounds. When one reacts, for example, one mole of a bis(2-hydroxyalkyl) alkylamine with at least one mole of a phosphite, the following compounds are possible. It will be understood that the structures are shown only to illustrate the types of compounds one can expect to find in the reaction product. It will also be understood that the mix of compounds in a particular reaction product will depend on the proportion of reactants.

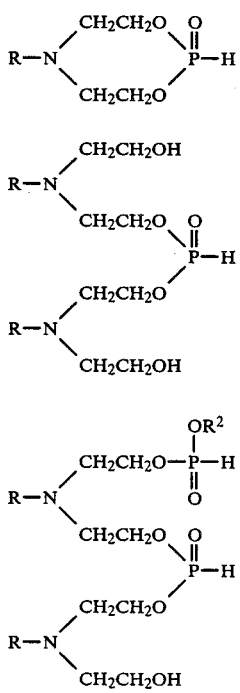

The isomer of III

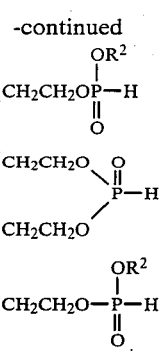

Polymers of III and IV    V

The lubricants contemplated for use with the amines herein disclosed include mineral and synthetic hydrocarbon oils of lubricating viscosity, mixtures of mineral oils and synthetic oils and greases from any of these, including the mixtures. The synthetic hydrocarbon oils include long-chain alkanes, such as cetanes, and olefin polymers such as oligomers of hexene, octene, decene, dodecene and the like. The phosphites are especially effective in synthetic oils formulated using mixtures of synthetic hydrocarbon olefin oligomers and lesser amounts of hydrocarbyl carboxylate ester fluids. The other synthetic oils, which can be used alone with the phosphorus compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons.

The compounds of the invention are used with lubricating oils or greases to the extent of from about 0.1% to about 10% by weight of the total composition, preferably from about 0.2% to about 2% and with fuels to the extent of from about 5 lbs. to about 250 lbs. per 1000 bbls. of fuel. Furthermore, other additives, such as detergents, antioxidants, antiwear agents and the like may be present. These can include phenates, sulfonates, polymeric succinimides, zinc dialkyl or diaryl dithiophosphates, polymers, calcium and magnesium salts, polymeric viscosity index improving additives such as olefin copolymers, sulfurized olefins and the like.

The following Examples will present illustrations of the invention. They are illustrative only, and are not meant to limit the invention.

EXAMPLE 1

Phosphite of Bis(2-Hydroxyethyl)oleylamine

Approximately 240 g of bis(2-hydroxyethyl)oleylamine (obtained as Ethomeen 0/12 from Armak Chemical Company) were charged to a one liter flask equipped with heater, agitator, provision for blanketing vapor space with nitrogen and Dean-Stark tube with condenser. Approximately 64 g of dimethyl phosphite were charged to the reactor. The reactor was heated to about 120° C. for 2 hours, 130° C. for 3 hours and 145° C. for three additional hours, after which methanol formation and condensation in the trap were observed to diminish and cease. The crude product was vacuum stripped at 155° C. to remove volatile materials. The product was an amber fluid when warm.

EXAMPLE 2

Partial Phosphite of Bis(2-Hydroyxethyl)cocoamine

Approximately 200 g of bis(2-hydroxyethyl)cocoamine (obtained as Ethomeen C/12 from Armak Chemical Co.) and 34 g of dimethyl phosphite were charged to a reactor equipped as generally described in Example 1. The reactor contents were heated to 120° C. for 2 hours, 140° C. for 3 hours and 150° C. for one hour, during which latter time evolution of methanol diminished and ceased. The crude product was then vacuum stripped at 155° C. to remove volatile materials. The warm product was a clear amber fluid.

EXAMPLE 3

Partial Phosphite of Bis(2-Hydroxyethyl)soyamine

Approximately 240 g of bis-(2-hydroxyethyl)soyamine (obtained as Ethomeen S/12 from Armak Chemical Co.) and 34 g of dimethyl phosphite were charged to a reactor equipped as generally described in Example 1. The reactor contents were heated to 120° C. for 2 hours, 140° C. for 3 hours and 150° C. for one hour, during which latter time evolution of methanol diminished and ceased. The crude product was then vacuum stripped at 150° C. for one hour to remove volatile materials. The warm product was a clear, amber product.

EXAMPLE 4

Partial Phosphite of Bis(2-Hydroxyethyl)oleylamine

Approximately 240 g of bis (2-hydroxylethyl)oleylamine of Example 1 and 34 g of dimethyl hydrogen phosphite were charged to a one liter reactor equipped as generally described in Example 1. The reactor contents were heated to 120° C. for 2 hours, 140° C. for 3 hours, and 152° C. for one hour, during which time evolution of methanol diminished and appeared to cease. The crude product was vacuum stripped at 152° C. for ½ hour to remove volatile materials. The warm product was a clear amber fluid.

EVALUATION OF PRODUCTS

The alkoxylated hydrocarbylamine derived phosphites were blended into fully formulated synthetic and mineral oil based automotive engine oil lubricants and evaluated using the Low Velocity Friction Apparatus Test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The results obtained are shown in Tables 1 and 2. The data in the tables are reported as percent reduction in coefficient of friction at two speeds. The friction-reducing ester additives were evaluated in a fully formulated mineral lubricating oil (Table 1) or 5W-30 synthetic lubricating oil (Table 2), each comprising an additive package including antioxidant, detergent and dispersant.

TABLE 1

| Friction Test Results Using Low Velocity Friction Apparatus | | |
|---|---|---|
| | Additive Conc. in Base Fluid | % Reduction in Coefficient of Friction at |
| | Weight % | 5 Ft/Min  30 Ft/Min |
| Base Oil A (fully formulated synthetic automotive engine oil containing detergent/dispersant/ inhibitor performance package) SAE 5W30 | — | 0     0 |
| Example 1 Plus Base Oil | 2 | 41    35 |
| Example 2 Plus Base Oil | 2 | 38    39 |
| | 1 | 24    30 |
| Example 3 Plus Base Oil | 2 | 24    26 |

TABLE 2

| Friction Test Results Using Low Velocity Friction Apparatus | | |
|---|---|---|
| | Additive Conc. in Base Fluid | % Reduction in Coefficient of Friction at |
| | Weight % | 5 Ft/Min  30 Ft/Min |
| Base Oil B (fully formulated mineral oil based automotive engine oil containing detergent/dispersant/ inhibitor performance package) SAE 10W40 | — | 0     0 |
| Example 3 Plus Base Oil Partial phosphite of bis-(2-hydroxyethyl) soyamine | 1 | 27    22 |

We claim:

1. A product of reaction made by reacting (1) an alkoxylated amine of the formula

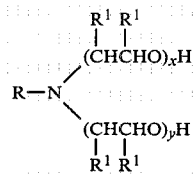

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (2) a phosphite of the formula

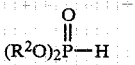

wherein $R^2$ is a $C_1$ to $C_6$ hydrocarbyl group, said reacting being carried out at a temperature between about 80° C. and about 200° C. and in reactant proportions such that from about 5 percent to about 100 percent of the amine hydroxy groups are reacted with said phosphite.

2. The product of claim 1 wherein the $C_6$ to $C_{30}$ hydrocarbyl group is alkyl, aryl, alkenyl, alkaryl, aralkyl or cycloalkyl.

3. The product of claim 1, wherein $R^1$ is an alkyl group.

4. The product of claim 1 wherein $R^2$ is an alkyl group.

5. The product of claim 1 wherein the alkoxylated amine is
2-hydroxylethylhexylamine, 2-hydroxyethyloctylamine,
2-hydroxyethyldodecylamine, 2-hydroxyethyltetradecylamine,
2-hydroxyethylpentadecylamine, 2-hydroxyethyleicosylamine,
2-hydroxyethyltriacontylamine, 2-hydroxyethyloleylamine,
2-hydroxyethyltallowamine, 2-hydroxyethylsoyamine,
bis(2-hydroxyethyl)hexylamine, bis(2-hydroxyethyl)octylamine,
bis(2-hydroxyethyl)dodecylamine, bis(2-hydroxyethyl)tetradecylamine,
bis(2-hydroxyethyl)pentadecylamine, bis(2-hydroxyethyl)eicosylamine,
bis(2-hydroxyethyl)triacontylamine, bis(2-hydroxyethyl)oleylamine,
bis(2-hydroxyethyl)tallowamine, bis(2-hydroxyethyl)soyamine,
2-hydroxylpropylhexylamine, 2-hydroxypropyloctylamine,
2-hydroxypropyldodecylamine, 2-hydroxypropyltetradecylamine,
2-hydroxypropylpentadecylamine, 2-hydroxypropyleicosylamine,
2-hydroxypropyltriacontylamine, 2-hydroxypropyloleylamine,
2-hydroxypropyltallowamine, 2-hydroxypropylsoyamine,
bis(2-hydroxypropyl)hexylamine, bis(2-hydroxypropyl)octylamine,
bis(2-hydroxypropyl)dodecylamine, bis(2-hydroxypropyl)tetradecylamine,
bis(2-hydroxypropyl)pentadecylamine, bis(2-hydroxypropyl)eicosylamine, bis(2-hydroxypropyl)triacontylamine, bis(2-hydroxypropyl)oleylamine,
bis(2-hydroxypropyl)tallowamine, bis(2-hydroxypropyl)soyamine or mixtures thereof.

6. The product of claim 1 wherein the phosphite is dimethyl phosphite, diethyl phosphite, dipropyl phosphite, dibutyl phosphite, diamyl phosphite, dihexyl phosphite or mixtures thereof.

7. The product of claim 1 wherein the alkoxylated amine is bis(2-hydroxyethyl)oleylamine and the phosphite is dimethyl phosphite.

8. The product of claim 1 wherein the alkoxylated amine is bis(2-hydroxyethyl)cocoamine and the phosphite is dimethyl phosphite.

9. The product of claim 1 wherein the alkoxylated amine is bis(2-hydroxyethyl)soyamine and the phosphite is dimethyl phosphite.

10. A lubricant composition comprising a major proportion of a lubricant selected from the group consisting of (1) mineral oil, (2) synthetic oil, (3) mixtures of synthetic oils; (4) mixtures of mineral oil and synthetic oil; and (5) grease from (1), (2), (3) or (4), and a friction reducing amount of a product made by reacting (1) an alkoxylated amine of the formula

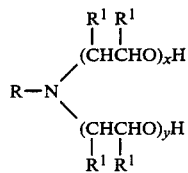

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (2) a phosphite of the formula

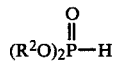

wherein R is a $C_1$ to $C_6$ hydrocarbyl group said reacting being carried out at a temperature between about 80° C. and about 200° C. and in reactant proportions such that from about 5 percent to about 100 percent of the amine hydroxy groups are reacted with said phosphite.

11. The composition of claim 10 wherein the $C_6$ to $C_{30}$ hydrocarbyl group is alkyl, aryl, alkeryl, alkaryl, aralkyl or cycloalkyl.

12. The composition of claim 10 wherein $R^1$ is an alkyl group.

13. The composition of claim 10 wherein $R^2$ is an alkyl group.

14. The composition of claim 10 wherein the alkoxylated amine
is 2-hydroxylethylhexylamine, 2-hydroxyethyloctylamine,
2-hydroxyethyldodecylamine, 2-hydroxyethyltetradecylamine,
2-hydroxyethylpentadecylamine, 2-hydroxyethyleicosylamine,
2-hydroxyethyltriacontylamine, 2-hydroxyethyloleylamine,
2-hydroxyethyltallowamine, 2-hydroxyethylsoyamine,
bis(2-hydroxyethyl)hexylamine, bis(2-hydroxyethyl)octylamine,
bis(2-hydroxyethyl)dodecylamine, bis(2-hydroxyethyl)tetradecylamine,
bis(2-hydroxyethyl)pentadecylamine, bis(2-hydroxyethyl)eicosylamine,
bis(2-hydroxyethyl)triacontylamine, bis(2-hydroxyethyl)oleylamine,
bis(2-hydroxyethyl)tallowamine, bis(2-hydroxyethyl)soyamine,
2-hydroxylpropylhexylamine, 2-hydroxypropyloctylamine,
2-hydroxypropyldodecylamine, 2-hydroxypropyltetradecylamine,
2-hydroxypropylpentadecylamine, 2-hydroxypropyleicosylamine,
2-hydroxypropyltriacontylamine, 2-hydroxypropyloleylamine,
2-hydroxypropyltallowamine, 2-hydroxypropylsoyamine,
bis(2-hydroxypropyl)hexylamine, bis(2-hydroxypropyl)octylamine,
bis(2-hydroxypropyl)dodecylamine, bis(2-hydroxypropyl)tetradecylamine,
bis(2-hydroxypropyl)pentadecylamine, bis(2-hydroxypropyl)eicosylamine,
bis(2-hydroxypropyl)triacontylamine, bis(2-hydroxypropyl)oleylamine,
bis(2-hydroxypropyl)tallowamine, bis(2-hydroxypropyl)soyamine or mixtures thereof.

15. The composition of claim 10 wherein the phosphite is dimethyl phosphite, diethyl phosphite, dipropyl phosphite, dibutyl phosphite, diamyl phosphite, dihexyl phosphite or mixtures thereof.

16. The composition of claim 10 wherein the alkoxylated amine is bis(2-hydroxyethyl)oleylamine and the phosphite is dimethyl phosphite.

17. The composition of claim 10 wherein the alkoxylated amine is bis(2-hydroxyethyl)cocamine and the phosphite is dimethyl phosphite.

18. The composition of claim 10 wherein the alkoxylated amine is bis(2-hydroxyethyl)soyamine and the phosphite is dimethyl phosphite.

19. The composition of claim 10 wherein the lubricant is (1) a mineral oil, (2) a synthetic oil or mixtures of synthetic oils, (3) a mixture of (1) and (2) and (4) a grease from (1), (2) or (3).

20. The composition of claim 19 wherein the lubricant is a mineral oil.

21. The composition of claim 19 wherein the lubricant is a synthetic oil or mixtures of synthetic oils.

22. The composition of claim 19 wherein the lubricant is the mixture of (3).

23. The composition of claim 19 wherein the lubricant is said grease.

24. The composition of claim 10 wherein said liquid fuel is a liquid hydrocarbon or a liquid alcohol.

25. A method of reducing fuel consumption in an internal combustion engine which comprises lubricating said engine with a lubricant composition comprising a major proportion of a lubricant selected from the group consisting of (1) mineral oil, (2) synthetic oil, (3) mixtures of synthetic oils; (4) mixtures of mineral oil and synthetic oil; and (5) grease from (1), (2), (3) or (4), and a fuel reducing amount of a product made by reacting (1) an alkoxylated amine of the formula

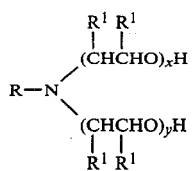

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (2) a phosphite of the formula

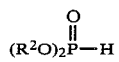

wherein R is a $C_1$ to $C_6$ hydrocarbyl group said reacting being carried out at a temperature between about 80° C. and about 200° C. and in reactant proportions such that from about 5 percent to about 100 percent of the amine hydroxy groups are reacted with said phosphite.

* * * * *